United States Patent
Chan et al.

(10) Patent No.: US 8,795,360 B2
(45) Date of Patent: Aug. 5, 2014

(54) CAM ACTION DETACHMENT FOR TRACHEOSTOMY TUBE

(75) Inventors: Sam C. Chan, Atlanta, GA (US); Nathan C. Griffith, Roswell, GA (US); Michael A. Kenowski, Alpharetta, GA (US); James F. Schumacher, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1307 days.

(21) Appl. No.: 12/603,859

(22) Filed: Oct. 22, 2009

(65) Prior Publication Data

US 2011/0098687 A1 Apr. 28, 2011

(51) Int. Cl.
*A61F 2/20* (2006.01)
*A61M 29/00* (2006.01)
*A61M 16/04* (2006.01)
*A61M 25/00* (2006.01)
*A61B 17/00* (2006.01)

(52) U.S. Cl.
CPC ....... *A61M 16/0472* (2013.01); *A61M 16/0434* (2013.01); *A61M 16/0465* (2013.01); *A61M 25/00* (2013.01); *A61B 2017/0046* (2013.01); *A61M 16/0497* (2013.01); *A61M 29/00* (2013.01)
USPC .................................................. 623/9; 606/1

(58) Field of Classification Search
CPC .......... A61F 19/00; A61F 1/267; A61F 2/203
USPC ............................... 623/9; 128/200.24; 606/1
See application file for complete search history.

(56) References Cited

U.S. PATENT DOCUMENTS

| 4,657,510 A * | 4/1987 | Gittleman ...................... 433/173 |
| 5,067,496 A | 11/1991 | Eisele |
| 5,421,325 A | 6/1995 | Cinberg et al. |
| 6,588,426 B2 | 7/2003 | Linderoth |
| 2007/0106122 A1 * | 5/2007 | Yokota et al. ................. 600/188 |
| 2008/0091211 A1 * | 4/2008 | Gately ............................ 606/99 |
| 2010/0012130 A1 * | 1/2010 | Guerra ..................... 128/207.15 |
| 2010/0288272 A1 * | 11/2010 | Yokota et al. ............ 128/200.26 |
| 2012/0245606 A1 * | 9/2012 | Goldberg et al. ............. 606/153 |

FOREIGN PATENT DOCUMENTS

| CA | 2 182 266 C | 4/2006 |
| CN | 101146565 A | 3/2008 |
| DE | 101 40 292 A1 | 3/2003 |
| EP | 2 065 629 A1 | 6/2009 |

(Continued)

*Primary Examiner* — Suzette J Gherbi
(74) *Attorney, Agent, or Firm* — James B. Robinson (57) ABSTRACT

There is provided a mechanism for gently detaching a loading catheter from a tracheostomy tube once the tube is placed in the trachea of a patient. After dilating the trachea, a loading catheter is inserted into a tracheostomy tube with which it desirably engages. Once the loading catheter and tracheostomy tube are attached to each other, the entire unit is passed through the stoma until the flange of the tracheostomy tube is in contact with the throat. The loading catheter may then be removed by rotating or twisting the loading catheter handle. The loading catheter and tracheostomy tube have a cam-action mechanism that gently forces the two parts apart as they are rotated relative to each other. This "cam action" disengagement allows for the removal of the loading catheter without subjecting the trachea or throat to undue pressure or forces that might cause trauma or increase recovery time. Other accessories like cannulas and obturators may attach and detach from the tracheostomy tube in a like manner.

6 Claims, 13 Drawing Sheets

(56) References Cited

FOREIGN PATENT DOCUMENTS

| JP | 2003-126259 A | 5/2003 |
| JP | 2004-033532 A | 2/2004 |
| WO | WO 2008/034872 A1 | 3/2008 |

\* cited by examiner

CAM ACTION DETACHMENT FOR TRACHEOSTOMY TUBE

Intubation with a tracheostomy tube may be performed by making a small horizontal incision in the skin of the neck to grant access to the trachea, dilating the opening and inserting the tube. A number of systems have been developed to accomplish the successful placement of the tube, including, for example the system developed by Cook Medical Inc utilizing the Blue Rhino® dilator (see also U.S. Pat. No. 6,637,435). In the Cook system, initial dilation is performed with the Blue Rhino® dilator. After dilation, the Blue Rhino® dilator is removed and the tracheostomy tube is introduced over a guide catheter using a second, "loading dilator" that fits just inside the trachostomy tube. The guide catheter, second dilator and tracheostomy tube are advanced into the trachea through the stoma in the tracheal wall as a unit. Once the tracheostomy tube is at the proper depth, the second dilator, guide catheter and guide wire are removed through the tracheostomy tube. An inner cannula is inserted into the tracheostomy tube and the tube connected to the ventilator and placed in service.

The Cook system does not positively attach the loading dilator to the tracheostomy tube, instead relying on friction and the resistance of the tracheal stoma to the advancement of the tube to keep the tracheostomy tube and loading dilator in firm contact with each other. Should the medical professional installing the tube pull back on the loading catheter before the tube is fully installed, it is certainly possible that the loading catheter will pull out of the tube and leave the tube partially installed, instead of being withdrawn as desired.

A positive connection system between the loading catheter and the tube would be desirable since it would allow greater control over the tube as it is being placed in the patient's neck. Such a connection system, however, must be easily and smoothly releasable. If it is not, excessive force may be required, increasing the risk of damaging the tracheal stoma or damaging the soft tissues of the walls of the trachea by contacting them in a forceful manner with the distal end of the tracheostomy tube.

There remains a need for a device that provides more control in the placement of a tracheostomy tube than prior art devices and that provides a positive connection between the loading dilator (or catheter) and the tracheostomy tube, and yet is easily an smoothly releasable.

SUMMARY

There is provided a novel detachment system for a tracheostomy tube and other devices like a dilator loading catheter. The mechanism gently detaches a loading catheter from a tracheostomy tube once the tube is placed in the trachea of a patient. Once the tracheal stoma is dilated, a loading catheter is inserted into a tracheostomy tube with which it desirably engages and, once the loading catheter and tracheostomy tube are attached to each other, the entire unit is passed through the stoma until the flange of the tracheostomy tube is in contact with the skin of the throat. The loading catheter may then be removed by rotating or twisting the loading catheter handle. The loading catheter and tracheostomy tube have a cam-action mechanism that gently forces the two parts apart as they are rotated relative to each other. This "cam action" disengagement allows for the removal of the loading catheter without subjecting the trachea or throat to undue pressure or forces that might cause trauma or increase recovery time. It is important that disconnection of the loading catheter from the tube be done in as gentle a manner possible to avoid trauma to the throat and trachea.

Once the tracheostomy tube is in place, other accessories may be connected to the tube in the same manner as the loading catheter from time to time for specific procedures. The disclosed mechanism uses cam-action surfaces to slowly move the attached part and the tube away from one another. The increasing linear separation of the two parts due to the rotationally increasing non-alignment of their respective, formerly mating surfaces is known as "cam action". More simply stated, a cam is a device that translates rotational movement into linear movement. When the two parts are rotated relative to each other, the cam-action shapes act together to "cam" or move their respective parts linearly apart.

BRIEF DESCRIPTION OF THE DRAWINGS

FIG. 14 is a drawing of the proximal end of the tracheostomy tube 26, with the view into the ventilation connection 72.

FIGS. 15 A and B are drawings of the interaction of complementary sinusoidally shaped cams on an obdurator and trach tube without showing the flange.

DETAILED DESCRIPTION

Tracheostomy is a lifesaving procedure to allow a patient to be ventilated directly through the trachea. Tracheostomy is also believed by many to prevent or retard the onset of ventilator acquired pneumonia (VAP). This lifesaving procedure, unfortunately, is relatively time consuming and current technology requires a large number of steps and pieces of equipment that must remain sterile and functioning properly in order to arrive at a successful conclusion. The tracheostomy procedure requires the creation of a stoma in the trachea, dilation of the stoma, and placement of the tracheostomy tube.

As mentioned above, once the tracheostomy tube is in place, other accessories may also be connected to the tube in the same manner as the loading catheter from time to time for specific procedures. The term "accessories" as used herein is meant to include any subordinate or supplementary parts that are used with a trach tube. Exemplary accessories include loading catheters, cannulas, obturators and other respiratory attachments.

The initial creation of the stoma is usually performed with a "punch dilator" or other sharp instrument that makes a small hole through the skin and tissues of the trachea and into the trachea. A dilator is used to enlarge this initial puncture.

Figure 1:
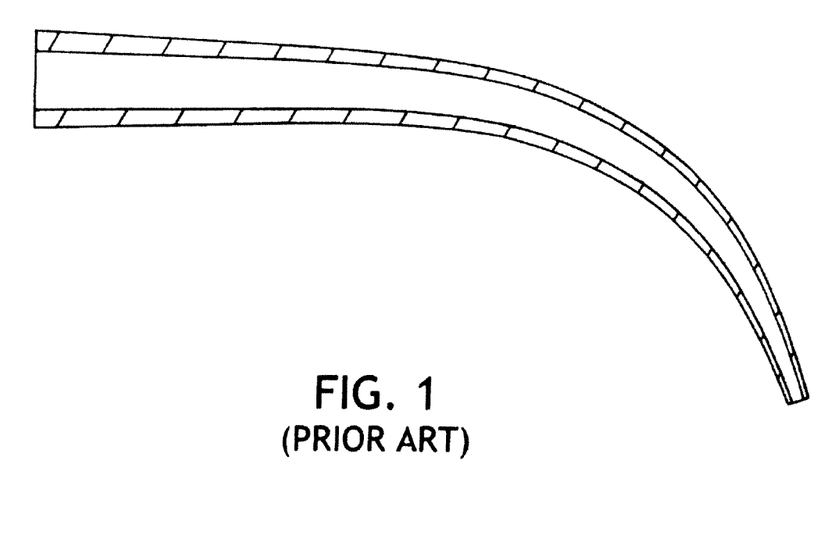
FIG. 1 is a drawing of the prior art Blue Rhino® dilator.

Dilators are instruments or substances for enlarging a canal, cavity, blood vessel or opening, according to the American Heritage Stedman's Medical dictionary 2001. FIG. 1 is a drawing of the prior art dilator from Cook Medical Inc. known as the Blue Rhino® dilator (see also U.S. Pat. No. 6,637,435). The '435 patent describes a one piece dilator having a generally linear shaft and a short distal tip portion with a curved tapered portion in between.

Another type of dilator is one disclosed in U.S. patent application Ser. No. 12/147,817, for example. In one embodiment of this type of dilator, for example, the dilator 10 has a body 20 and a distal tip 12 (FIG. 2) with an inner portion 18. The dilator 10 has at least two parts or pieces wherein the tip 12 is detachably attached to the body 20. The body 20 is shown in FIG. 3 and has a marking line 22 or alternatively a ridge where the diameter is approximately 42 French which serves as a depth marking or insertion stopping point for the dilation procedure.

Still other dilators may be available to increase the stoma size in preparation for the insertion of the tracheostomy tube. For example, a series of graduated dilators, each larger than the one before, may be used one after another to gradually increase the stoma size. This procedure is somewhat time consuming, but may nonetheless be successfully done.

Once the dilation of the stoma is satisfactory, the tracheostomy tube is installed in the trachea, in most cases using a loading catheter. Loading catheters are used to support the tracheostomy tube as it is being inserted so that it does not bend or fold. The loading catheter also typically provides a handle for the health care professional to use in guiding the tracheostomy tube into position.

Figure 3:
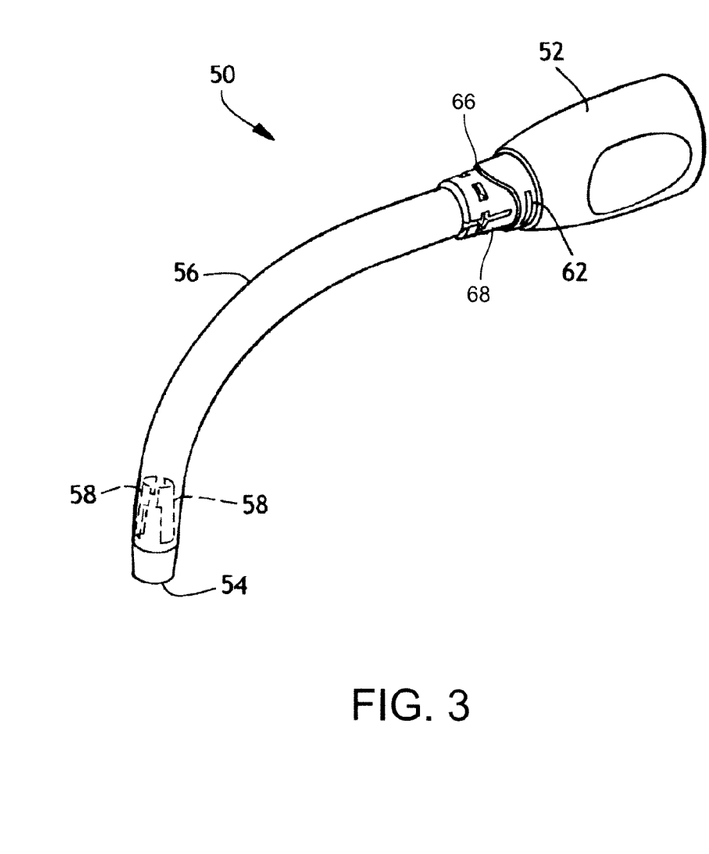
FIG. 3 is a drawing of a dilator loading catheter 50.

FIG. 3 shows one example of a loading catheter 50. In this embodiment, the loading catheter desirably has a handle 52 that is freely rotatable relative to the midsection 56 at the proximal end of the loading catheter 50 and a tip 54 at the distal end. The handle 52 need not be able to rotate an entire 360 degrees but is should move sufficiently to disengage the lock mechanism used to attach the loading catheter 50 to the tracheostomy tube 26, as discussed below. The loading catheter handle 52 also has a cam-action mechanism, in this case a circumferential ridge 66, located on the distal end of the handle 52. The cam-action ridge 66 is used to disconnect the loading catheter 50 from the tracheostomy tube 26 and will be discussed in greater detail below.

In the embodiment of FIG. 3, the handle 52 also has tabs 62 on either side that are sized to detachably engage corresponding slots 64 in the tracheostomy tube 26 to hold the handle 52 and tube 26 together. It should be noted that other detachable means of attaching the tracheostomy tube to the dilator or other accessories may be used as well. The handle 52 cannot rotate freely in relation to the cam-action ridge 66 or the tabs 62 as they are desirably one single piece. The midsection 56 (between the handle 52 and tip 54) may be tubular and is flexible so that it can bend as it is inserted and removed from the tracheostomy tube 26. Suitable materials for the midsection 56 are softer plastics like polyurethanes and some polyolefins. Suitable materials for the tip 54 and handle 52 are somewhat harder plastics like nylons and some polyolefins. The device must be biocompatible, desirably free of di(2-ethylhexyl) phthalate (DEHP) and preferably free of animal derived products. Polyvinyl chloride may also be used to fabricate the components.

Figure 2:
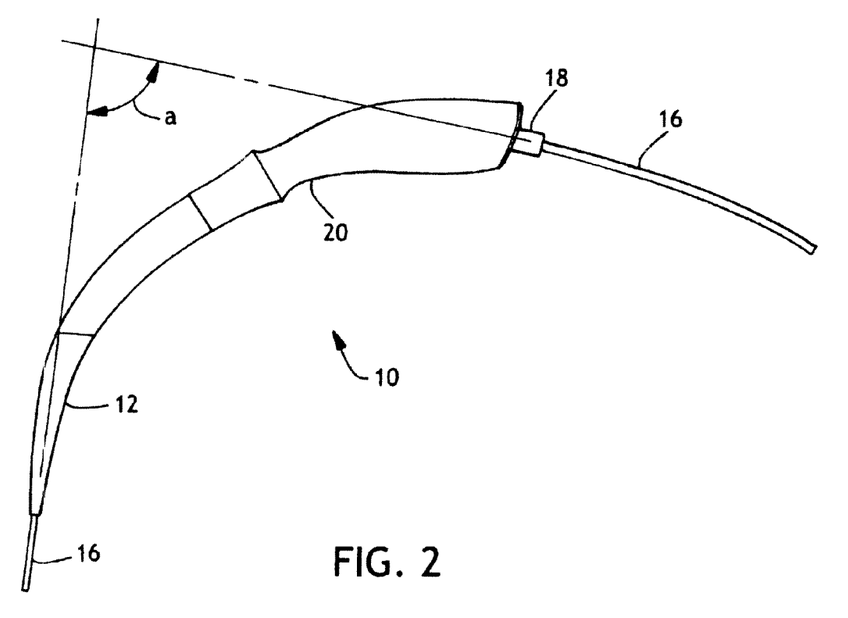
FIG. 2 is a drawing of a tapered dilator.

The embodiment of FIG. 3 is designed to attach to a tip of a dilator that is allowed to remain in the dilated stoma as described in patent application Ser. No. 12/147,817. It should be noted that the dilator with a tip that separates is described herein merely as an illustration of one embodiment and as stated above, the cam-action mechanism may be used with many different dilators and other accessories. When used with a dilator with a tip that separates, the loading catheter tip 54 shown in FIG. 3 has a mechanism on its distal end for attaching it to the proximal end 28 of the dilator tip 12 (FIG. 2). One type of distal end attachment mechanism that may be used is locking arms or snap detents 58 located within or near the distal end or catheter tip 54. The mechanism for engaging the loading catheter 50 to the tip 12 may be detachable but is more desirably not detachable since a firm connection is desired to ensure that the tip 12 does not separate from the loading catheter 50 as the tip 12 is being withdrawn through the tube 26, as described in more detail below.

Figure 4:
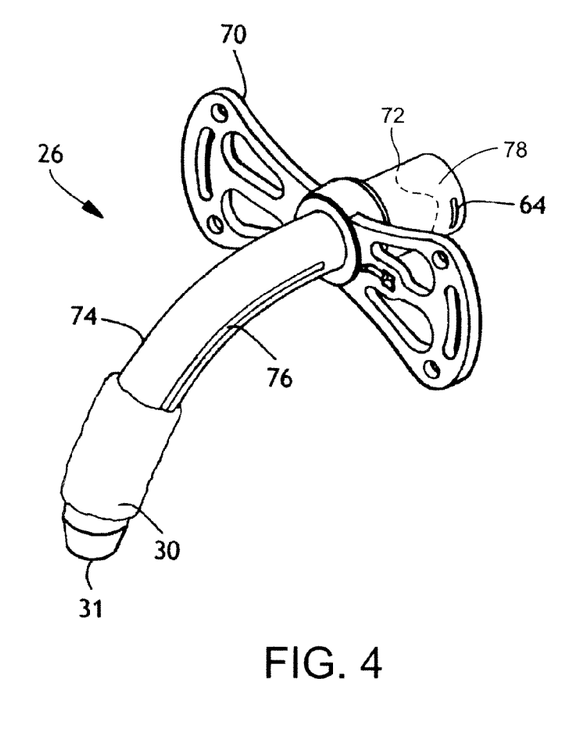
FIG. 4 is a drawing of the trachestomy tube 26 showing the flange for attachment to the throat and shown with the cannula removed.

One embodiment of a tracheostomy tube is shown in FIG. 4. There is a flange 70 on the tracheostomy tube 26 on the proximal end that is used to attach the tracheostomy tube to a patient's throat. The flange 70 extends on either side of the tube 26 near the proximal end where the ventilator connection 72 is located. The flange 70 is desirably flexible and non-irritating and can be sutured onto the throat of a patient to anchor the tube 26. The size of the flange will vary depending on the size and needs of the patient. The ventilator connection 72 has a cam-action mechanism, in this case a ridge 78, shown as a dashed line in FIG. 4 and discussed in greater detail below. The tube 26 has slots 64 on either side sized to engage the tabs 62 on the loading dilator 50, though, as noted above, other means of detachably engaging the tube and loading catheter or other accessories may be used. The tube 26 also has a hollow shaft 74 extending from the proximal end to the distal end 31. An inflation line 76 runs from the proximal end to the balloon cuff 30 so that the cuff may be inflated to obdurate the trachea. The tracheostomy tube is desirably made from a plastic material that has sufficient flexibility to allow the slots 64 and tabs 62 to disengage when the cam-action mechanism is used. Suitable materials include thermoplastic polyurethane elastomers, thermoplastic polyolefin elastomers, thermoplastic polyolefin block copolymers, SBS di-block elastomers, SEBS tri-block elastomers, polyvinyl chloride, polyethylene terephthalate and blends and mixtures thereof. A particularly suitable polymer is polyurethane.

Figure 5:
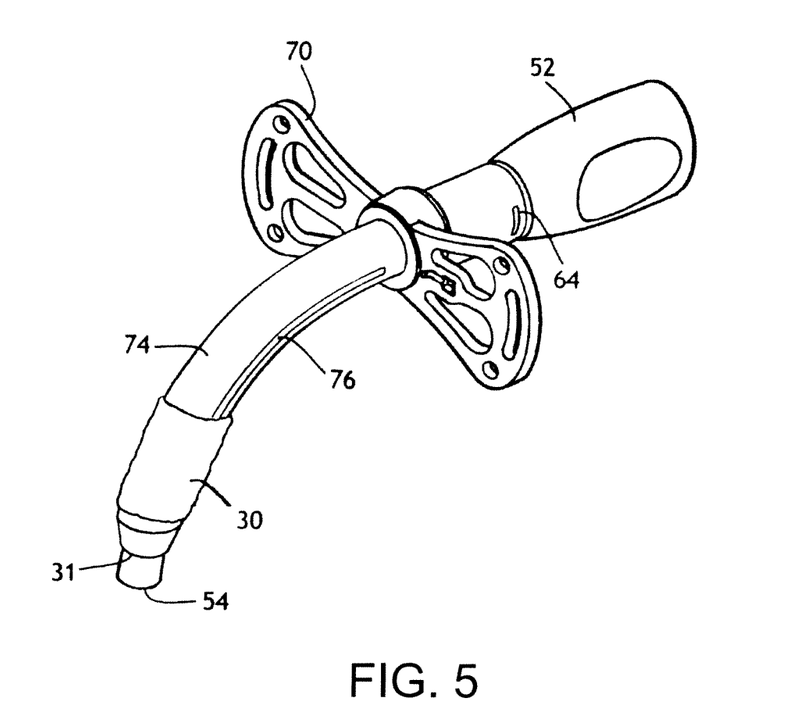
FIG. 5 is a drawing of a loading catheter 50 installed in the tracheostomy tube 26.

In order to use this embodiment, the loading catheter 50 is slid into the tracheostomy tube 26 (FIG. 5). The loading catheter handle 52 detachably engages the proximal end of the tracheostomy tube 26 with, for example, a slot 64 and tab 62 arrangement as shown in FIGS. 3 and 4 where there are tabs 62 on both sides of the handle 52 which mate with slots 64 on the proximal end of the tracheostomy tube 26. At the same time, the complementary cam-action mechanism ridges 66, 78 mate with one another. Once the tabs 62 and slots 64 engage, the loading catheter 50 and tracheostomy tube 26 are held together as a single unit. Once the cam-action ridges 66, 78 are mated to one another, the handle is not freely rotatable as it is held in place by the engaged ridges and tabs. The tracheostomy tube 26 with the loading catheter 50 attached is inserted into the stoma.

Figure 6:
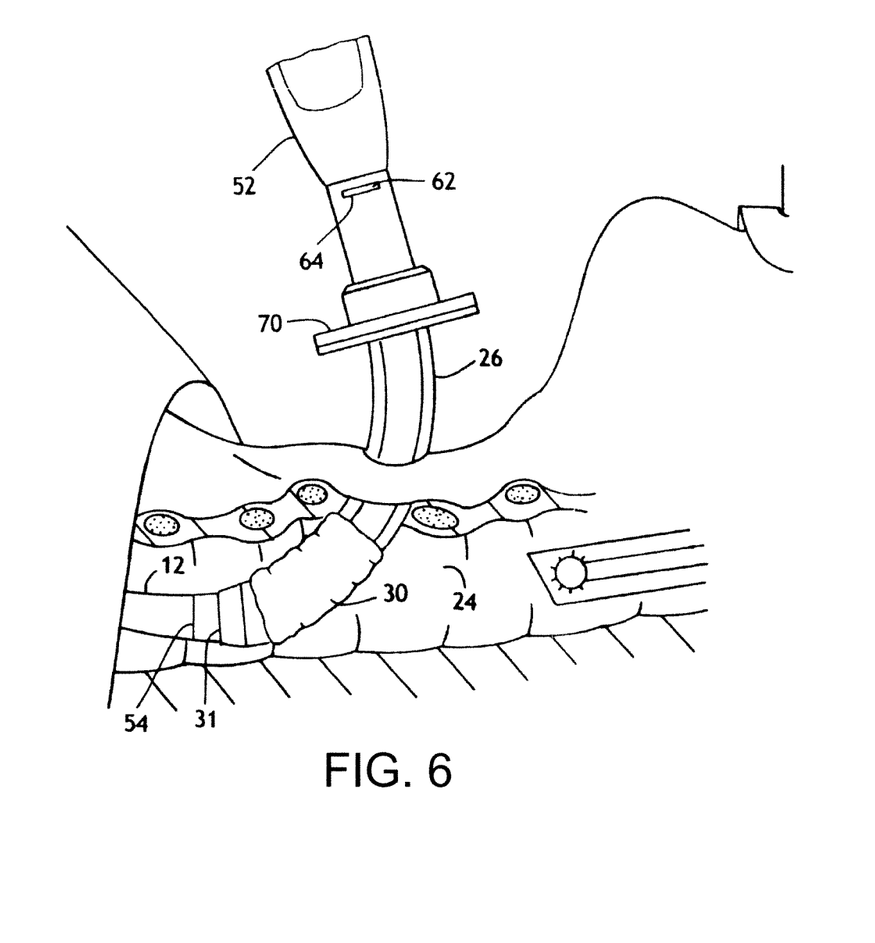
FIG. 6 is a drawing of the position of the tube 26, loading catheter 50 and tip 12 as they are passed into the trachea as a unit.
Figure 7:
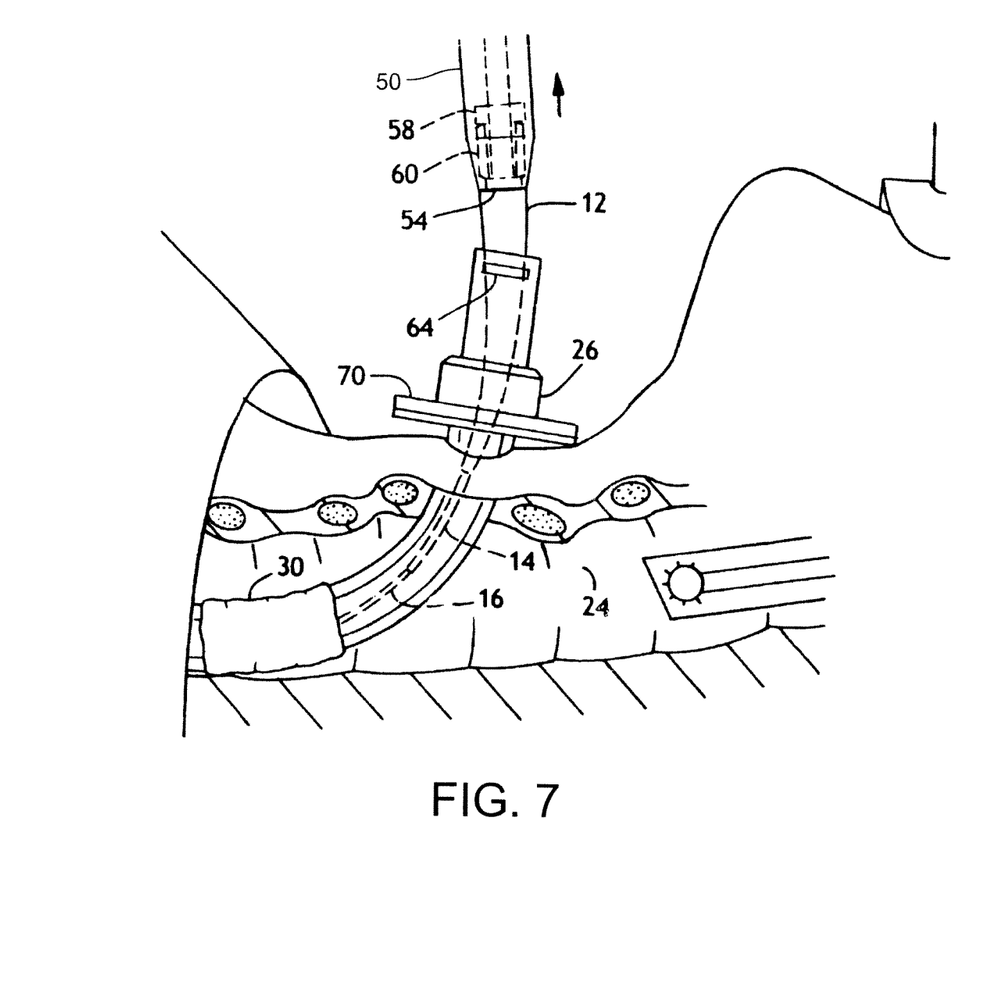
FIG. 7 is a drawing of a loading catheter, dilator tip, guiding catheter and J-wire being withdrawn through the tracheostomy tube with the tube remaining in place in the trachea.
Figure 8:
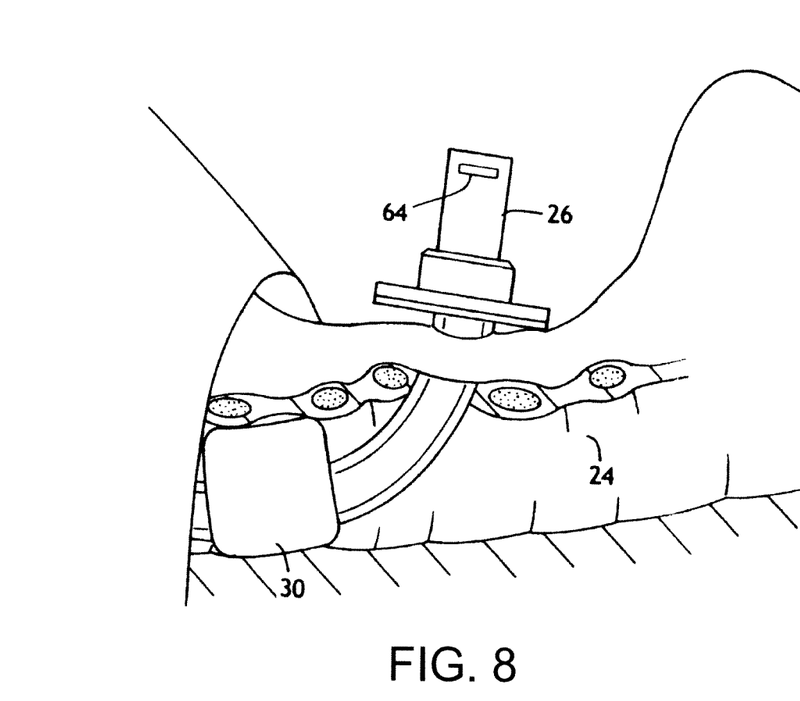
FIG. 8 is a drawing of the tracheostomy tube in its final position in the trachea, with the tracheostomy cuff inflated.

In the case of the dilator having the detachable tip 12 as described above, the loading catheter 50 is passed along the guide wire until it engages the proximal end 28 of the tip 12. The tip 12, loading catheter 50 with handle 52 visible, and tracheostomy tube 26 are then passed into the trachea 24 as a unit (FIG. 6) to the point where the flange 70 on the tube 26 rests against the throat. Once the tube 26 is in place in the trachea 24, the loading catheter 50 with the attached tip 12, guiding catheter 14 and J-wire 16 may be withdrawn through the tracheostomy tube 26 (FIG. 7) with only the tube 26 remaining in place in the trachea 24 (FIG. 8).

In the case of dilators without detachable tips and that are fully removed from the stoma prior to insertion of the tracheostomy tube, the loading catheter may have a more pronounced or rounded distal end 54 extending beyond the distal tip of the tracheostomy tube 32, in order to smoothly enter the stoma. The cam-action mechanism described herein is suitable for use on loading catheters and tracheostomy tubes after any type of dilation is performed.

Withdrawing the loading catheter 50 and any other attached parts may be accomplished by disengaging the detachably attached handle 52 from the proximal end of the tracheostomy tube 26 and pulling the handle 52 away from the tube 26. It is important that the loading catheter 50 smoothly and gently disconnect from the tracheostomy tube 26 but that they remain firmly connected until it is desired to disconnect them. An abrupt or violent disconnection can cause trauma to the tissue of the throat and trachea surrounding the tracheostomy tube.

The cam-action mechanism for disconnecting the two parts will now be described in greater detail.

Turning again to FIG. 3, it can be seen that the loading catheter 50 has a cam-action circumferential ridge 66 that is located on the handle 52 near the tabs 62. The ridge 66 as shown in FIG. 3 is sinusoidally shaped and has two high points and two low points in the typical sinusoidal wave shape as it travels around the handle, though more or fewer high and low points may be used. FIG. 4 shows that the inner surface of the ventilation connection 72 of the tracheostomy tube 26 also has a cam-action ridge 78 shaped to be complementary to the shape of the ridge of the loading catheter 50. When the two parts (the tracheostomy tube and loading catheter) are joined, the loading catheter ridge 66 and tracheostomy tube ridge 78 are mated, shown as a dashed line in FIG. 5.

It should be noted that although a sinusoidal shape is shown in the Figures for illustrative purposes, any suitable cam shape may be used. For example, a saw tooth, zig zagging shape may be used. Furthermore, the shape of the ridge need not be symmetrical around the circumference. As a further example; the shape may be sinusoidal on one half of the wave only and abruptly drop on the other (downward) half so that the handle can only be turned in one direction in a manner similar to a ratcheting mechanism. The exact shape of the ridge 66 is not critical as long as it functions as a cam-action mechanism to linearly (axially) separate the two parts in response to rotational motion.

Figure 9:
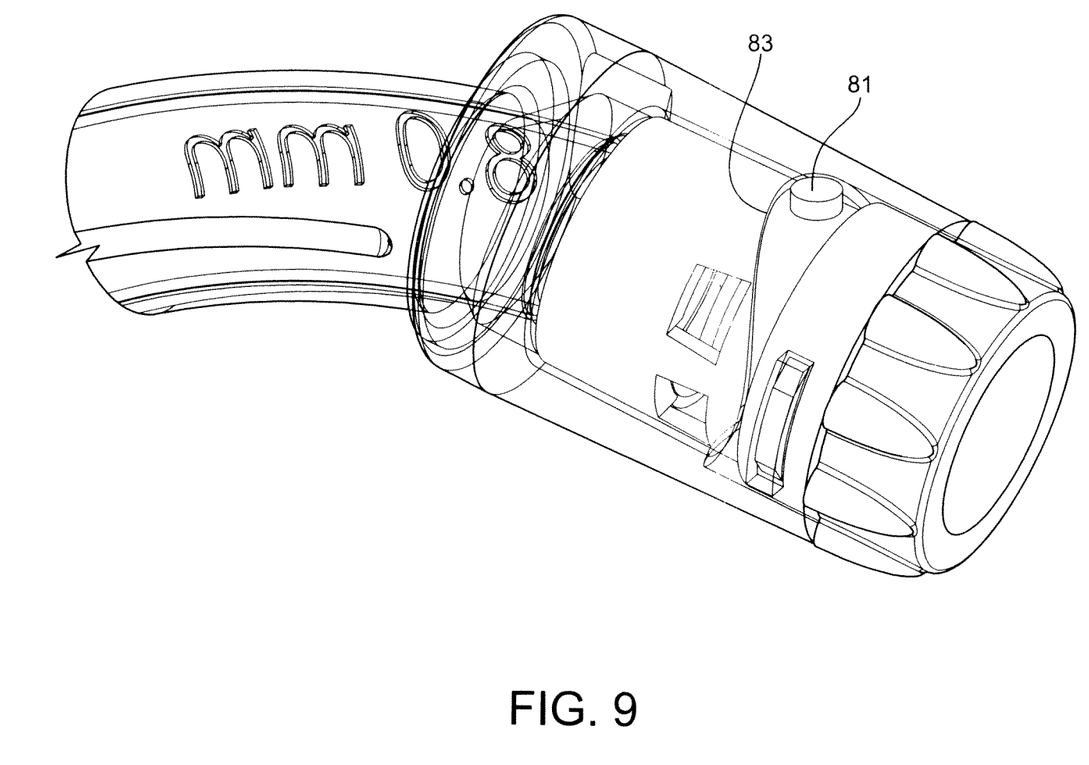
FIG. 9 is a drawing of a cam-action mechanism using a pin to guide the parts apart.
Figure 10:
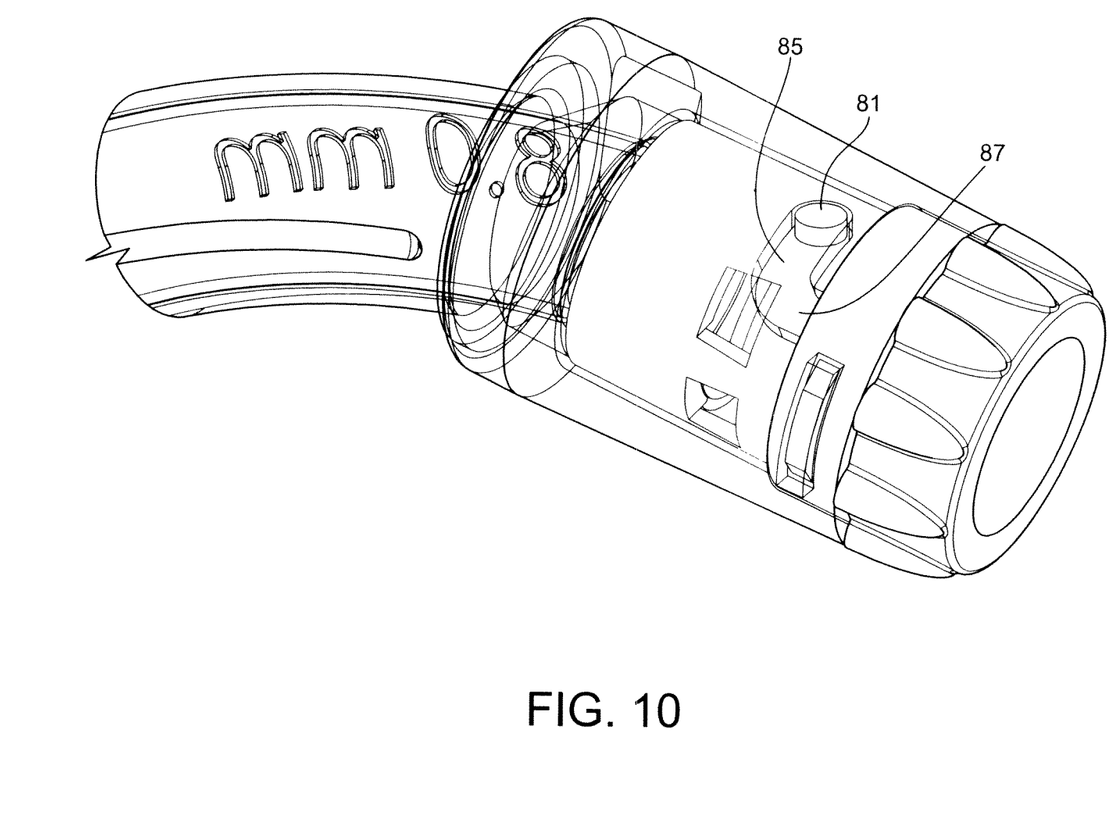
FIG. 10 is a drawing of a cam-action mechanism using a slot to guide the parts apart.

Still other embodiments of the cam-action mechanism include assemblies wherein one of the ridges is replaced with a pin, knob, tab or other protrusion 81 that can ride on the remaining ridge 83 (FIG. 9) to produce the linear separation in response to rotational motion. Yet another embodiment replaces one ridge with a slot or recessed track 85 in the same shape as the ridge (FIG. 10) and the corresponding ridge is replaced with a pin, knot, tab or other protrusion 81 that fits into the slot. The protrusion moves in the slot in a cam-action motion that linearly separates the two parts. At some point in the slot, desirably the closest point to the other part, the slot must have a gap 87 to allow the protrusion to leave the slot so the two parts can completely separate. More simply, the cam-action mechanism may be a two part assembly like, for example, a pin and a slot (FIG. 9), a protrusion and a ridge (FIG. 10), and complementary ridges where the accessory and the tracheostomy tube each have one of the two assembly parts.

In the embodiments of the cam-action mechanism using a ridge 66, the ridge 66 is desirably about a millimeter higher than the immediately adjacent distal part 68 of the handle 52, though it may be a greater or lesser height if desired. The peak to trough height of the cam-action circumferential ridge 66 may be between 1 and 8 mm, more particularly between 2 and 6 mm and still more particularly about 3 mm. If a sinusoidal shape is used, the greater the amplitude of the sine wave the faster the parts will detach, but the greater the force that will be needed to affect separation.

Figure 11:
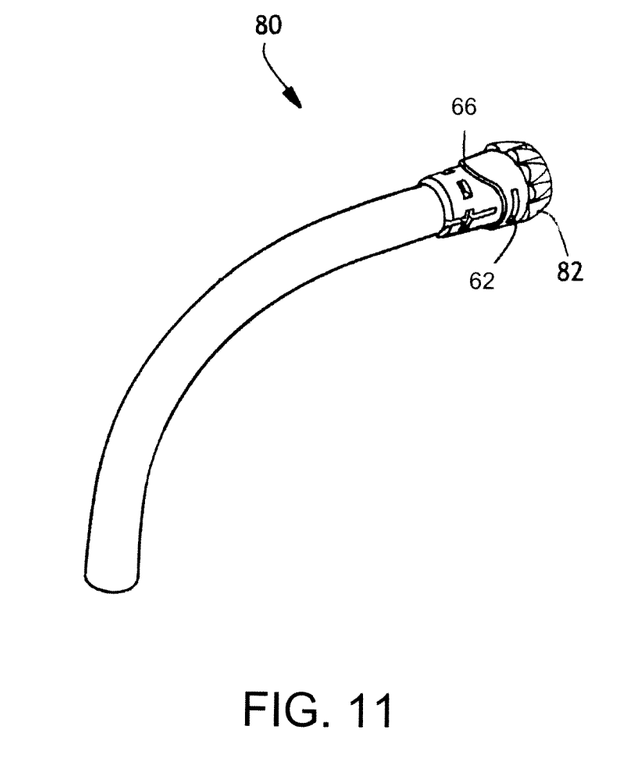
FIG. 11 is a drawing of the replaceable (e.g. disposable) cannula for use with the tracheostomy tube.
Figure 12:
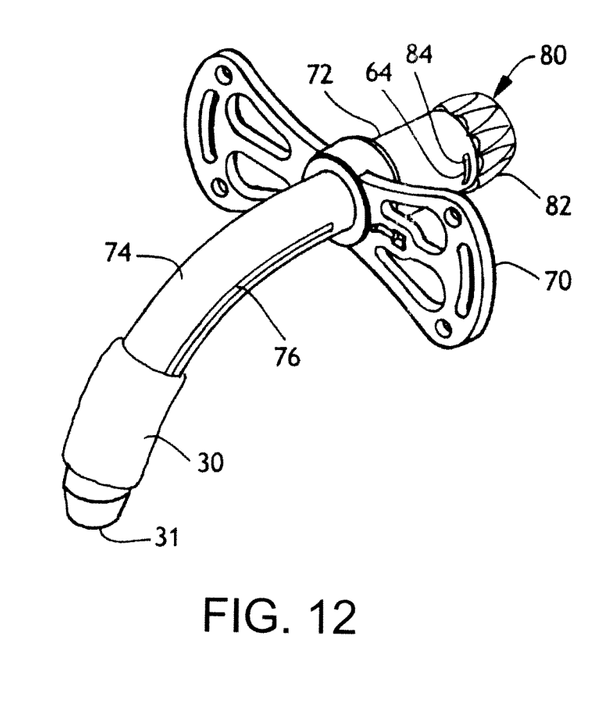
FIG. 12 is a drawing of the tracheostomy tube showing the replaceable cannula installed in the tube.

FIG. 11 shows a disposable cannula 80 that may be placed within the tracheostomy tube from the proximal end (shown installed in FIG. 12). The inner cannula 80 may be attached to the tracheostomy tube 26 in a manner identical to the attachment of the loading catheter 50, i.e., using tabs 62 that mate with the slots 64 on the tube exposing only the cannula end 82 on the proximal end. In like manner, the disposable 80 has a cam-action ridge 66 that is virtually identical to the ridge 66 found on the loading catheter 50 and which is used to disengage the cannula 80 from the tube 26. These disposable cannulas 80 are changed regularly so that bacterial growth is kept to a minimum. The cannulas are made from a plastic material such as a polyolefin, polyurethane, nylon, etc and are desirably flexible. Cannulas may be treated with anti-bacterial and/or anti-viral coatings or other active materials to help reduce the growth of harmful organisms. The cannula distal end is either flush with the tracheostomy tube distal end 31 or extends a very short distance beyond.

Figure 13:
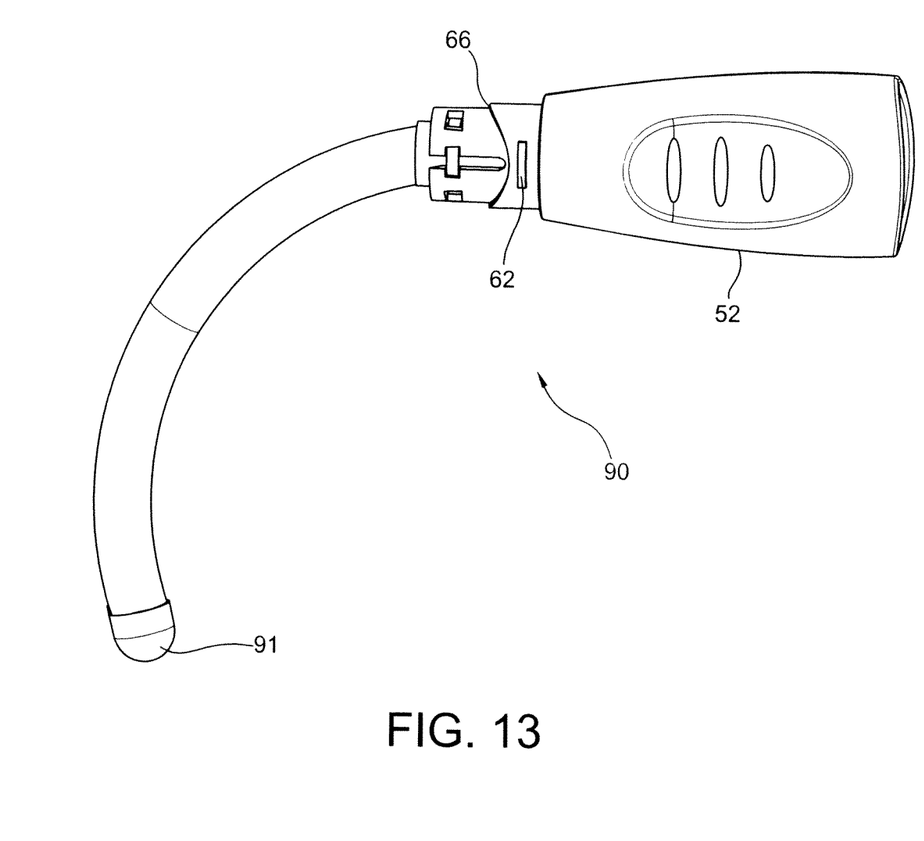
FIG. 13 is a drawing of an obturator having a cam-action ridge on its proximal end, within a trach tube.

In addition to the loading catheter and disposable cannula, this cam-action mechanical system may be used on any other accessory that is desired to be connected to the tracheostomy tube. As shown in FIG. 13, an obturator 90 for use in placing tracheostomy tubes, for example, may be produced with any of the suitable embodiments of the cam-action mechanism described above. Such an obturator 90 may be used to replace a tracheostomy tube 26 in a patient, a situation that arises after a tube has been in place for a period of time. Obturators 90 for the tracheostomy tube replacement procedure generally have a rounded tip 91 that barely protrudes from the end of the tracheostomy tube once the obturator is inserted into the tracheostomy tube, since a new stoma and dilation are not required. Obturators 90 are otherwise quite similar to loading catheters 50 in that they have handles 52, a ridge 66 and tabs 62. In the procedure, the old tracheostomy tube is removed from the patient using an obturator 90 and the new, usually smaller one is installed using another obturator 90. The obturator 90 can be removed from the tracheostomy tube 26 using the cam-action detachment mechanism described herein.

Figures 14, 15A:
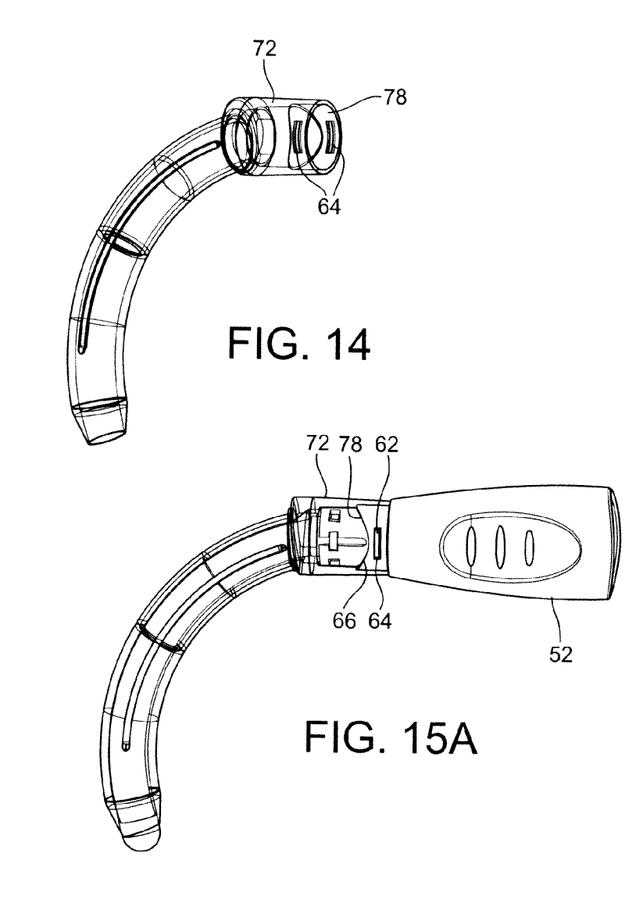

As described above, the inner surface of the ventilation connection 72 of the exemplary tracheostomy tube 26 has a cam-action ridge 78 shaped to be complementary to the shape of the ridges of accessories like the loading catheter 50, the cannulas 80, obturator 90. FIG. 14 shows a view into the proximal end of the ventilation connection 72. The tracheostomy tube ridge 78 is desirably about a millimeter higher than the immediately adjacent inner surface of the tube 26 though it may be a greater or lesser height if desired. The peak to trough height of the cam-action circumferential ridge 78 may be between 1 and 8 mm. The ridge 78 as shown in FIG. 14 has two high points and two low points in a typical sinusoidal wave shape as it travels around the interior of the ventilator connector 72, though more or fewer high and low points may be used. The diameters of the tube 26, loading catheter 50 and cannula 80 are sized so that the corresponding cam-action ridges are maintained in contact with one another while the parts are engaged.

Figure 15B:
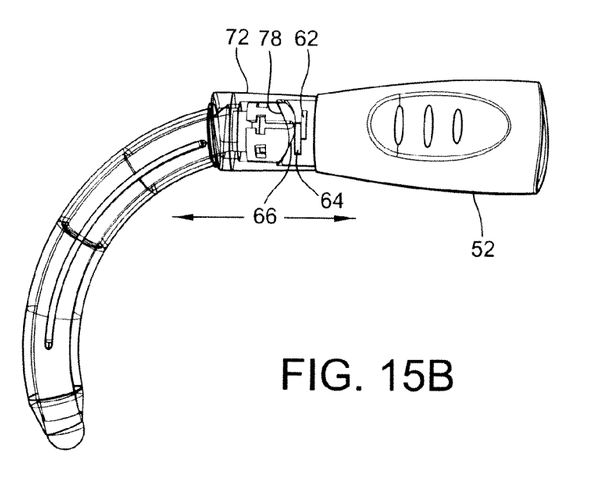

When the corresponding parts are engaged using the slot 64 and tab 62, 84 arrangement as shown in FIGS. 3, 4 and 9, 10, the cam-action ridges 66, 86 on the loading catheter 50 and cannula 80 mate with the matching or complementary cam-action ridge 78 located on the inner surface of the tracheostomy tube 26. This mated arrangement is shown in FIG. 15A where the loading catheter handle 52 is visible on the right. When it is desired to remove the loading catheter 50 or cannula 80 from the tracheostomy tube 26, the respective part's proximal end is rotated (e.g. the handle 52). As the part to be removed is rotated, the cam-action ridges no longer mate completely with one another and as a result the two parts are slowly and gently moved away from one another as shown in FIG. 15B. This rotation and separation of the two parts gently forces the tabs 62, 84 to disengage from the slots 64. This separation flexes the parts somewhat in order to allow the tab to leave the slot, and the components must be sufficiently flexible to allow this to occur without breaking or other damage. Once the tabs and slots are no longer engaged, the part to be removed may be completely withdrawn from the tracheostomy tube 26.

The rotating or twisting action described above cams the loading catheter handle 52, for example, off the proximal end of the tracheostomy tube 26, overcoming any static friction that may exist in the system and defeating the tabs 62 and slots 64 locking the loading catheter handle 52 to the tube 26. This action allows the user to pull all the loading components out through the inner lumen of the tracheostomy tube 26, leaving only the tube 26 in place. (Clearly the tip 12 must be sized so that its largest diameter is slightly less than that of the tracheostomy tube 26 that it is intended to pass through.) Removal of the disposable cannulas 80 may be done in the same manner, i.e., by rotating the proximal end 82 relative to the tube 26 to cam the tab 84 out of the slot 64 and allow for withdrawal of the cannula 80 from the tube 26. The removal of the obturator occurs in a like manner.

The use of cam action allows for the relatively gentle removal of the loading catheter or cannula from the tracheostomy tube and so helps to reduce the stress on the stoma site and the resultant trauma and increased recovery time.

The tracheostomy tube 26 has a balloon cuff 30 around its circumference on a lower (distal) portion of the tube that serves to block the normal air flow in the trachea so that (assisted) breathing takes place through the tracheostomy tube using a ventilator. The cuff is desirably made from a soft, pliable polymer such as polyurethane, polyethylene teraphihalate (PETP), low-density polyethylene (LDPE), polyvinyl chloride (PVC), polyurethane (PU) or polyolefin. It should be very thin; on the order of 25 microns or less, e.g. 20 microns, 15 microns, 10 microns or even as low as 5 microns in thickness. The cuff should also desirably be a low pressure cuff operating at about 30 mmH$_2$O or less, such as 25 mmH$_2$O, 20 mmH$_2$O, 15 mmH$_2$O or less. Such a cuff is described in U.S. Pat. No. 6,802,317 which describes a cuff for obturating a patient's trachea as hermetically as possible, comprising: a cuffed balloon which blocks the trachea below a patient's glottis, an air tube, the cuffed balloon being attached to the air tube and being sized to be larger than a tracheal diameter when in a fully inflated state and being made of a soft, flexible foil material that forms at least one draped fold in the cuffed balloon when inflated in the patient's trachea, wherein the foil has a wall thickness below or equal to 0.01 mm and the at least one draped fold has a loop found at a dead end of the at least one draped fold, that loop having a small diameter which inhibits a free flow of secretions through the loop of the at least one draped fold. Another description of such a cuff is in U.S. Pat. No. 6,526,977 which teaches a dilator for obturating a patient's trachea as hermetically as possible, comprising a cuffed balloon which blocks the trachea below a patient's glottis, an air tube, the cuffed balloon being attached to the air tube and being sized to be larger than a tracheal diameter when in a fully inflated state and being made of a sufficiently soft, flexible foil material that forms at least one draped fold in the cuffed balloon when fully inflated in the patient's trachea, wherein the at least one draped fold formed has a capillary size which arrests free flow of secretions across the balloon by virtue of capillary forces formed within the fold to prevent aspiration of the secretions and subsequent infections related to secretion aspiration.

Exemplary sizes for the various components of the dilator removal device are as follows;

The distance from the flange 70 to the distal tip 31 of the tracheostomy tube 26 may be an arched distance of between 70 and 100 mm, desirably between about 75 and 95 mm and more desirably between 80 and 90 mm. The angle of the tracheostomy tube from the flange to the distal end is between 85 and 120 degrees, desirably between 95 and 115 degrees, more desirably between 100 and 110 degrees. The flange 70 may desirably be of a width between 6 and 12 cm and height of 1 to 6 cm, more particularly between 7 and 10 cm and 2 and 5 cm respectively or still more particularly between 8 and 9 cm and 2 and 4 cm respectively.

In one embodiment, a loading catheter 50 may desirably have a tubular midsection having a arched length between about 8 and 13 cm, particularly about 11 cm and may terminate as much as 20 mm beyond the distal tip of the tracheostomy tube or may terminate within it. The handle 52 may be between 2 and 7 cm long, particularly about 5 cm. The loading catheter distal end or tip 54 may be between 3 and 10 mm in inner diameter, particularly about 6 mm. In any event, the loading catheter midsection 56 and tip 54 and dilator tip 12 must be sized so that they will pass through the tracheostomy tube 26.

As will be appreciated by those skilled in the art, changes and variations to the invention are considered to be within the ability of those skilled in the art. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A system for removing an accessory from a tracheostomy tube comprising a ridge cam-action mechanism adapted to linearly separate the accessory and the tracheostomy tube in response to rotating said accessory and said tracheostomy tube relative to each other, wherein said cam-action mechanism is a two part assembly of complementary sinusoidal shaped ridges and said ridges are about a millimeter in height and said sinusoidal shapes have an amplitude of between 1 and 8 mm, and wherein the accessory and the tracheostomy tube each comprise one of the two assembly parts.

2. The system of claim 1 wherein said ridges are asymmetrical around the circumference.

3. The system of claim 2 wherein said ridges comprise half of a sinusoid in a proximal direction and abruptly drop on the other half, so that the accessory can only be turned in one direction.

4. A tracheostomy tube and mating accessory comprising a ridge cam-action mechanism to separate the tube and accessory from each other by rotating the tube and accessory relative to each other wherein said mechanism comprises a protrusion and a sinusoidally shaped ridge.

5. A tracheostomy tube and mating accessory comprising a ridge cam-action mechanism to separate the tube and accessory from each other by rotating the tube and accessory relative to each other wherein said tube and said accessory attach together with a tab and slot lock.

6. The tracheostomy tube and mating accessory of claim 5 wherein said cam-action mechanism forces said tab and slot apart.

\* \* \* \* \*